(12) United States Patent
Ta et al.

(10) Patent No.: US 12,414,868 B2
(45) Date of Patent: *Sep. 16, 2025

(54) INTRAVASCULAR STENT HAVING HIGH FATIGUE PERFORMANCE

(71) Applicant: Abbott Cardiovascular Systems Inc., Santa Clara, CA (US)

(72) Inventors: Diem Uyen Ta, San Jose, CA (US); Senthil K. Eswaran, Sunnyvale, CA (US); Nianjiong Joan Bei, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 18/375,298

(22) Filed: Sep. 29, 2023

(65) Prior Publication Data

US 2024/0130876 A1 Apr. 25, 2024
US 2024/0225866 A9 Jul. 11, 2024

Related U.S. Application Data

(60) Division of application No. 17/873,537, filed on Jul. 26, 2022, now Pat. No. 11,844,712, which is a division of application No. 16/669,206, filed on Oct. 30, 2019, now Pat. No. 11,426,296, which is a continuation of application No. 15/635,026, filed on Jun. 27, 2017, now Pat. No. 10,463,514.

(51) Int. Cl.
*A61F 2/915* (2013.01)
*A61F 2/89* (2013.01)

(52) U.S. Cl.
CPC ............... *A61F 2/915* (2013.01); *A61F 2/89* (2013.01); *A61F 2002/91533* (2013.01); *A61F 2002/91558* (2013.01); *A61F 2002/91566* (2013.01)

(58) Field of Classification Search
CPC .. A61F 2/915; A61F 2/89; A61F 2002/91558; A61F 2002/91533; A61F 2002/91566
See application file for complete search history.

(56) References Cited

U.S. PATENT DOCUMENTS

| | | | |
|---|---|---|---|
| 6,629,994 B2 | 10/2003 | Gomez et al. | |
| 9,089,412 B2 | 7/2015 | Kleiner | |
| 9,522,503 B2 | 12/2016 | Gale et al. | |
| 2002/0095207 A1 | 7/2002 | Moriuchi et al. | |
| 2003/0149469 A1* | 8/2003 | Wolinsky | A61F 2/915 623/1.11 |
| 2004/0133265 A1 | 7/2004 | Duffy | |
| 2020/0206004 A1 | 7/2020 | Lin et al. | |

* cited by examiner

*Primary Examiner* — Melanie R Tyson
*Assistant Examiner* — Rebecca Lynee Zimmerman
(74) *Attorney, Agent, or Firm* — Fulwider Patton LLP (57) ABSTRACT

This invention is directed to an expandable stent for implantation in a body lumen, such as an artery, and a method for making it from a single length of tubing. The stent consists of a plurality of radially expandable cylindrical elements generally aligned on a common axis and interconnected by one or more links. A Y-shaped member is comprised of a U-shaped member and a link having a curved portion and a straight portion to improve the flexibility and thereby improve the fatigue performance of the Y-link junction.

8 Claims, 5 Drawing Sheets

INTRAVASCULAR STENT HAVING HIGH FATIGUE PERFORMANCE

This application is a division of U.S. Ser. No. 17/873,537 filed Jul. 26, 2022, which is a division of U.S. Ser. No. 16/669,206 filed Oct. 30, 2019, now U.S. Pat. No. 11,426,296, issued Aug. 30, 2022, which is a continuation of U.S. Ser. No. 15/635,026 filed Jun. 27, 2017, now U.S. Pat. No. 10,463,514, issued Nov. 5, 2019, the entire contents of which are incorporated herein by reference.

BACKGROUND

This invention relates to expandable endoprosthesis devices, generally called stents, which are adapted to be implanted into a patient's body lumen, such as blood vessel, to maintain the patency thereof. These devices are very useful in the treatment of atherosclerotic stenosis in blood vessels.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

The stent must be able to satisfy a number of mechanical requirements. First, the stent must be capable of withstanding the structural loads, namely radial compressive forces, imposed on the stent as it supports the wall of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or a network of interconnecting structural elements often referred to, in the art, as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through the movement of individual structural elements in the pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Along with crimping and expansion forces, implanting the stent in the dynamic environment in a curved artery section causes stresses in the stent structure that can result in fatigue failure.

What has been needed and heretofore unavailable is a stent formed from a polymer material and modified in critical structural areas where cyclical loads are concentrated to reduce fatigue stresses in order to improve the fatigue performance of the stent.

SUMMARY OF THE INVENTION

The present invention is directed to a polymer expandable stent which is relatively flexible along its longitudinal axis to facilitate delivery through tortuous body lumens, but which has structural features to improve fatigue performance of the stent.

The stent of the invention generally includes a plurality of radially expandable cylindrical elements or rings which are relatively independent in their ability to expand and to flex relatively to one another. Typically, the individual radially expandable rings of the stent are dimensioned so as to be longitudinally shorter than their own diameters. Interconnecting elements or links are used to connect adjacent cylindrical rings and provide increased stability and are preferably positioned to provide longitudinal flexibility to the stent. The resulting stent structure is a series of radially expandable cylindrical rings which are spaced longitudinally close enough so that small dissections in the wall of a body lumen may be pressed back into position, but not so close as to compromise the longitudinal flexibility of the stent.

Each of the cylindrical rings making up the stent has a proximal end and a distal end and a cylindrical plane defined by a cylindrical outer wall surface that extends circumferentially between the proximal end and the distal end of the cylindrical ring. Generally the cylindrical rings have a serpentine or undulating shape which includes at least one U-shaped element, and typically each ring has more than one U-shaped element. The cylindrical rings are interconnected by at least one link which attaches one cylindrical ring to an adjacent cylindrical ring. The combination of the rings and links forms the stent pattern and allows the stent to be highly flexible along its longitudinal axis.

Not only do the links that interconnect the cylindrical rings provide flexibility to the stent, but the positioning of the links also enhances the flexibility by allowing uniform flexibility when the stent is bent in any direction along its longitudinal axis. Uniform flexibility along the stent derives in part from the links in one ring being circumferentially offset from the links in an adjacent ring. Further, the cylindrical rings are configured to provide flexibility to the stent in that portions of the rings can flex or bend as the stent is delivered through a tortuous vessel.

The cylindrical rings typically are formed of a plurality of peaks and valleys, where the valleys of one cylindrical ring are circumferentially aligned with the valleys of an adjacent cylindrical ring, which is known in the art as being in-phase. In this configuration, at least one link attaches each cylindrical ring to an adjacent cylindrical ring so that at least a portion of the link is positioned within one of the valleys, and it attaches the valley to an adjacent valley.

While the cylindrical rings and links generally are not separate structures, they have been conveniently referred to as rings and links for ease of identification. Further, the cylindrical rings can be thought of as comprising a series of U, W and Y-shaped structures in a repeating pattern. Again, while the cylindrical rings are not divided up or segmented into U's, W's and Y's, the pattern of the cylindrical rings resembles such configurations. The U's, W's and Y's promote flexibility in the stent primarily by flexing as the stent is delivered through a tortuous vessel.

The radial expansion of the expandable rings deforms the undulating pattern thereof similar to changes in a waveform which result in decreasing the waveform's amplitude. Preferably, the undulating patterns of the individual cylindrical structures are in phase with each other in order to prevent contraction of the stent along its length when it is expanded. The cylindrical structures of the stent are plastically deformed when expanded so that the stent will remain in the expanded condition, and therefore they must be sufficiently rigid when expanded to prevent the collapse thereof in use.

The links may be formed in a unitary structure with the expandable cylindrical rings from the same intermediate product, such as a tubular element. Preferably, all of the links of a stent are joined at the valleys of the undulating structure of the cylindrical rings which form the stent. In this manner, there is no shortening of the stent upon expansion.

The number and location of the links interconnecting adjacent cylindrical rings can be varied in order to develop the desired longitudinal flexibility in the stent structure both in the unexpanded as well as the expanded condition. These properties are important to minimize alteration to the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

In one embodiment, the Y-shaped members are formed by the links attaching to the curved portion of a valley, which then resembles the Y-shaped member. In this embodiment, each link has a straight section and a curved section. The curved section extends in a circumferential direction. The curved section has a first curved length and a second curved length, the first curved length being greater than the second curved length. Further, the straight section has a length, and the curved section has a length with the length of the curved section being greater than the length of the straight section. The curved section in the links greatly improves the fatigue resistance of the links, especially at the interface of the curved section and the valley of a cylindrical ring.

Other features and advantages of the present invention will become more apparent from the following detailed description of the invention, when taken in conjunction with the accompanying exemplary drawings.

DETAILED DESCRIPTION OF THE PREFERRED EMBODIMENTS

Figure 1:
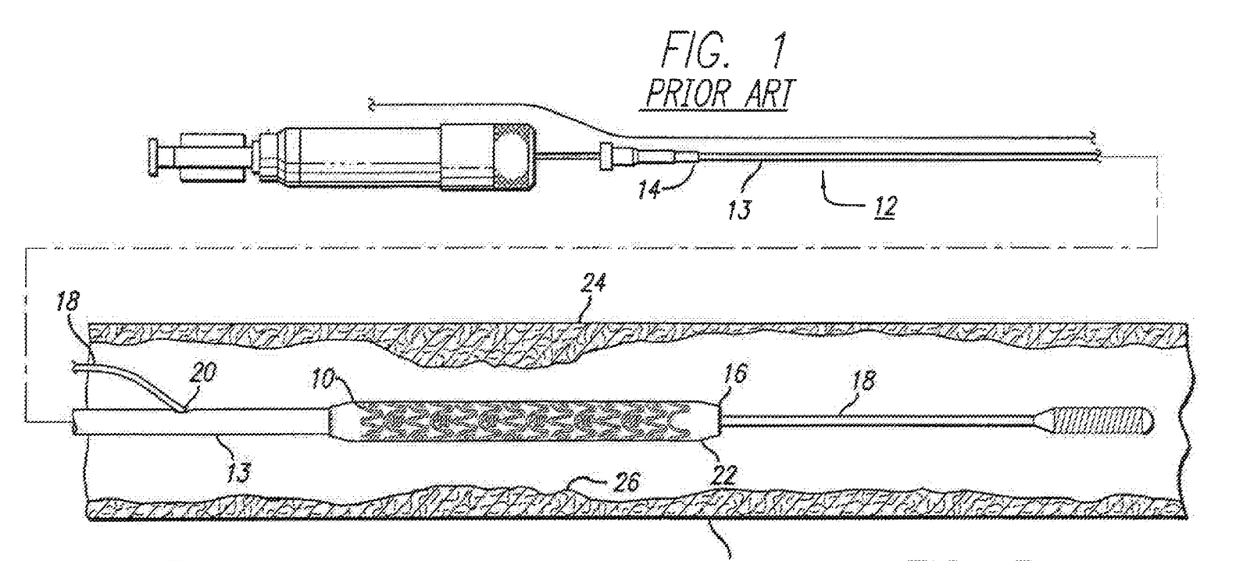
FIG. 1 is an elevational view, partially in section, of a prior art stent with curved links.

Turning to the drawings, FIG. 1 depicts a prior art stent 10 mounted on a conventional catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire 18 by any of the well-known methods of an over the wire system (not shown) or a well-known rapid exchange catheter system, such as the one shown in FIG. 1.

Catheter assembly 12 as depicted in FIG. 1 is of the well-known rapid exchange type which includes an RX port 20 where the guide wire 18 exits the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 is used to repair a diseased or damaged arterial wall which may include the plaque 26 as shown in FIG. 1, or a dissection, or a flap which are sometimes found in coronary arteries, peripheral arteries and other vessels.

In a typical procedure to implant prior art stent 10, the guide wire 18 is advanced through the patient's vascular system by well-known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire 18 so that the stent is positioned in the target area. The expandable member or balloon 22 is inflated by well-known means so that it expands radially outwardly and in turn expands the stent radially outwardly until the stent is apposed to the vessel wall. The expandable member is then deflated, and the catheter is withdrawn from the patient's vascular system.

Figure 2:
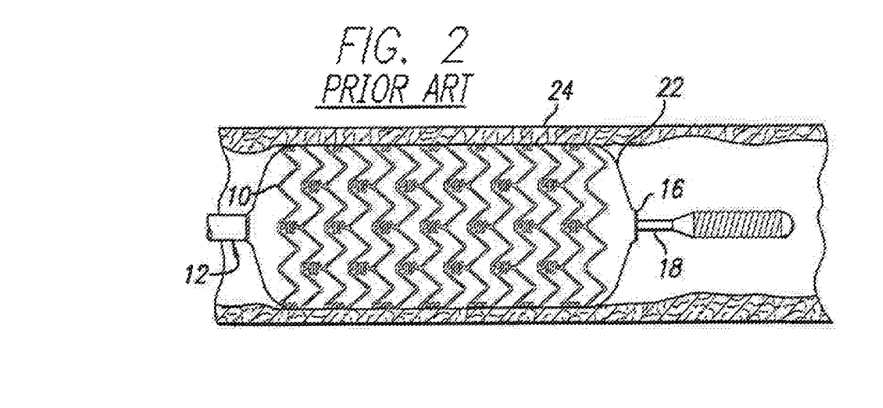
FIG. 2 is an elevational view, partially in section, similar to that shown in FIG. 1 wherein the prior art stent is expanded within an artery.

The guide wire typically is left in the lumen for post-dilatation procedures, if any, and subsequently is withdrawn from the patient's vascular system. As depicted in FIG. 2, the balloon is fully inflated with the prior art stent expanded and pressed against the vessel wall, and in FIG. 3, the implanted stent remains in the vessel after the balloon has been deflated, and the catheter assembly and guide wire have been withdrawn from the patient.

Figure 3:
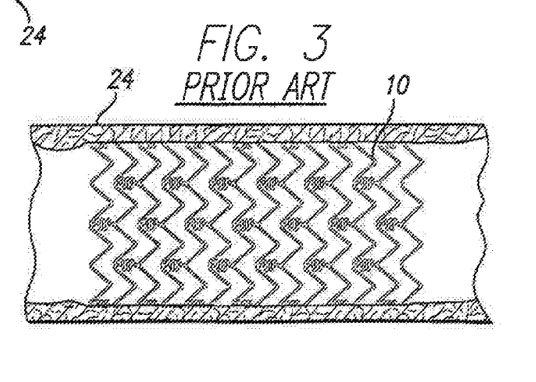
FIG. 3 is an elevational view, partially in section, showing the expanded prior art stent implanted in the artery after withdrawal of the delivery catheter.

The prior art stent 10 serves to hold open the artery after the catheter is withdrawn, as illustrated by FIG. 3. Due to the formation of the stent from a thin walled tubular member, the undulating components of the stent are relatively flat in transverse cross-section so that when the stent is expanded, they are pressed into the wall of the artery and, as a result, do not interfere with the blood flow through the artery. The stent is pressed into the wall of the artery and will eventually be covered with endothelial cell growth which further minimizes blood flow interference. Plastic deformation of the undulating rings of the stent during expansion provides good tacking characteristics to prevent stent movement within the artery. Furthermore, the closely spaced cylindrical elements at regular intervals provide uniform support for the wall of the artery and consequently are well adapted to tack up and hold in place any small flaps or dissections in the wall of the artery.

Figure 4:
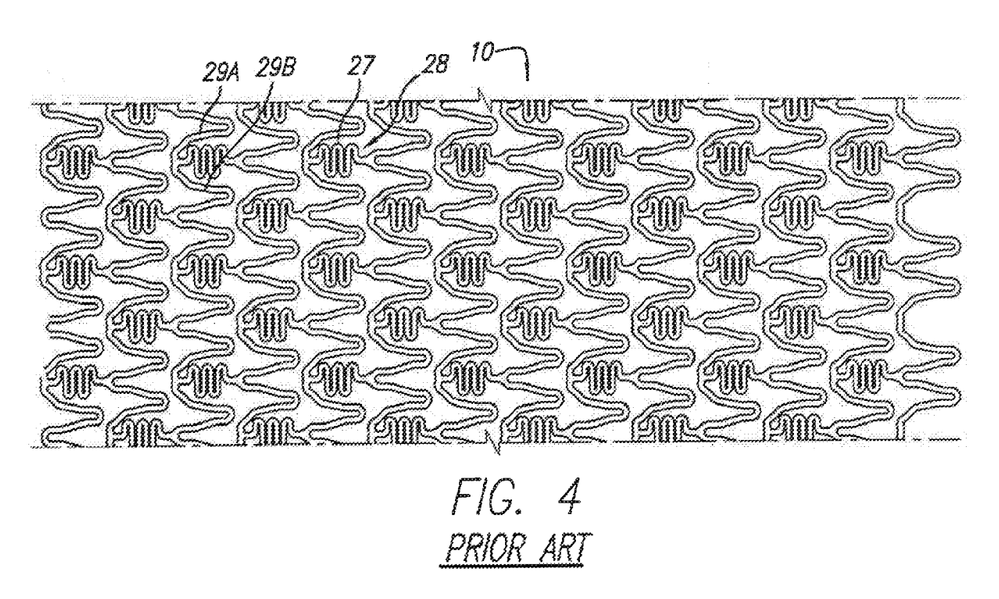
FIG. 4 is a plan view of a flattened prior art stent which illustrates the curved links of the stent shown in FIG. 5.
Figure 5:
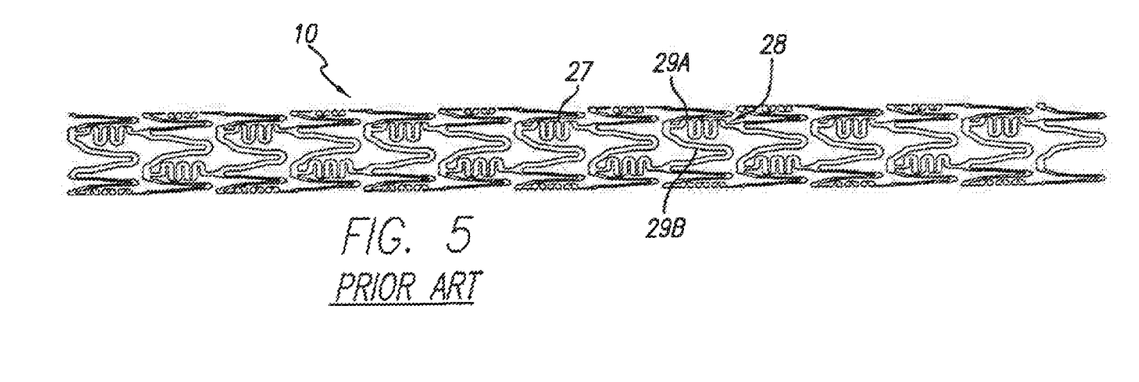
FIG. 5 is a plan view of the prior art stent of FIG. 4 in an unexpanded state.

One of the problems associated with some prior art stents such as the one shown in FIG. 4 is the ability to more tightly crimp or compress the stent 10 onto the balloon portion of the catheter. For example, the undulating portion 27 of the links 28 of the prior art stent in FIG. 4 is positioned between two struts 29A and 29B so that as the stent can only be tightly crimped or compressed onto the balloon portion of the catheter before contact between the undulating portion of the link and the struts is made. Preferably, the undulating portion of the link and the adjacent struts should not overlap, therefore the undulating portion of the link limits the amount of the crimping or compression of each cylindrical ring onto the balloon portion of the catheter. The present invention solves this problem and allows for a tightly compressed or crimped stent onto the catheter. Further, since the stent is formed from a polymer material, there may be some deformation of the curved link during crimping and/or expansion.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for the surface of a device can be a biodegradable polymer or combination of biodegradable polymers, a biostable polymer or combination of biostable polymers, or a combination of biodegradable and biostable polymers.

A stent may be fabricated from a polymeric tube or a polymeric sheet by rolling and bonding the sheet edges to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a stent pattern on a tube.

The pattern of a stent can vary throughout its structure to allow radial expansion and compression and longitudinal flexure. A pattern may include portions of struts that are straight or relatively straight, or some patterns may include bending elements. The bending elements can comprise of bending elements such as W-shaped bending elements and Y-shaped bending elements. Bending elements that have a U-shape are free bending elements. The free bending elements are not directly connected to any adjacent ring, whereas each W-shaped bending element is directly connected by one of the links at a concave portion of the apex of the W-shaped bending element to a convex portion of an apex on an adjacent ring located in a direction of a first end of a scaffold, and each Y-shaped bending element is directly connected by one of the links at a convex portion of the apex of the Y-shaped bending element to a concave portion of an apex on an adjacent ring located in a direction of a second end of the scaffold.

Bending elements bend inward when a stent is crimped to allow for radial compression. Bending elements also bend outward when a stent is expanded to allow for radial expansion. After deployment, a stent is under static and cyclic compressive loads from the vessel wall. Thus, bending elements are subjected to deformation during use. "Use" includes, but is not limited to, manufacturing, assembling (e.g., crimping stent on a catheter), delivery of stent into and through a bodily lumen to a treatment site, deployment of stent at a treatment site, and treatment after deployment.

As indicated above, a stent is required to have certain mechanical requirements. A stent must have sufficient radial strength to withstand structural loads, namely radial compressive forces, imposed on the stent as it supports the wall of a vessel. In addition, the stent must possess sufficient flexibility to allow for crimping, expansion, and cyclic loading. Also, a sufficiently low profile, that includes crimped diameter and strut thickness, is important. As the profile of a stent decreases due to the stent being crimped more tightly on the balloon and/or thinner strut thickness, as the strut thickness decreases, its delivery to the treatment site is easier, and the disruption to the blood flow caused by the strut thickness decreases.

Polymers tend to have a number of shortcomings for use as materials for stents. One such shortcoming is that many biodegradable polymers have a relatively low modulus, and thus relatively low radial strength. Compared to metals, the strength to weight ratio of polymers is smaller than that of metals. A polymeric stent with inadequate radial strength can result in mechanical failure or recoil inward after implantation into a vessel. To compensate for the relatively low modulus, a polymeric stent requires significantly thicker struts than a metallic stent, which results in an undesirably large profile.

Another shortcoming of polymers is that many polymers, such as biodegradable polymers, tend to be brittle under physiological conditions or conditions within a human body. Specifically, such polymers can have a Tg, which is defined below, above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of its use, i.e., crimping, delivery, deployment, and post-deployment during a desired treatment period.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised, the actual molecular volume in the sample remains constant, and so a higher coefficient of expansion points to an increase in free volume associated with the system and therefore increases freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Other potential problems with polymeric stents include creep, stress relaxation, and physical aging. Creep refers to the gradual deformation that occurs in a polymeric construct subjected to an applied load. It is believed that the delayed response of polymer chains to stress during deformation causes creep behavior. Creep occurs even when the applied load is constant. Creep can cause an expanded stent to retract radially inward, reducing the effectiveness of a stent in maintaining desired vascular patency. The rate at which polymers creep depends not only on the load, but also on temperature. In general, a loaded construct creeps faster at higher temperatures.

Stress relaxation is also a consequence of delayed molecular motions as in creep. Contrary to creep, however, which is experienced when the load is constant, stress relaxation occurs when deformation (or strain) is constant and is manifested by a reduction in the force (stress) required to maintain a constant deformation Physical aging, as used herein, refers to densification in the amorphous regions of a semi-crystalline polymer. Physical aging of semi-crystalline polymers that have glass transition temperatures (Tg) above their normal storage temperature, which, for the purposes of this invention is room temperature, i.e., from about 15° C. to about 35° C., occurs primarily through the phenomenon known as densification. Densification occurs when polymer chains rearrange in order to move from a non-equilibrium state to an equilibrium state. The reordering of polymer chains tends to increase the modulus of the polymer resulting in a brittle or more brittle polymer.

Thus, physical aging results in an increase in brittleness of a polymer which can result in cracking of struts upon crimping and deployment. Since physical aging results from densification of amorphous regions of a polymer, an increase in crystallinity can reduce or inhibit physical aging.

However, it is well known by those skilled in the art that the mechanical properties of a polymer can be modified through various processing techniques, such as, by applying stress to a polymer. James L. White and Joseph E. Spruiell, Polymer and Engineering Science, 1981, Vol. 21, No. 13. The application of stress can induce molecular orientation along the direction of stress which can modify mechanical properties along the direction of applied stress. For example, strength and modulus are some of the important properties that depend upon orientation of polymer chains in a polymer. Molecular orientation refers to the relative orientation of polymer chains along a longitudinal or covalent axis of the polymer chains.

A polymer may be completely amorphous, partially crystalline, or almost completely crystalline. A partially crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions. An oriented amorphous region also tends to have high strength and high modulus along an axis of alignment of polymer chains. Additionally, for some polymers under some conditions, induced alignment in an amorphous polymer may be accompanied by crystallization of the amorphous polymer into an ordered structure. This is known as stress induced crystallization.

As indicated above, due to the magnitude and directions of stresses imposed on a stent during use, it is important for the mechanical stability of the stent to have suitable mechanical properties, such as strength and modulus, in the axial and circumferential directions. Therefore, it can be advantageous to modify the mechanical properties of a tube, to be used in the fabrication of a stent, by induced orientation from applied stress in the axial direction, circumferential direction, or both. Since highly oriented regions in polymers tend to be associated with higher strength and modulus, it may be desirable to incorporate processes that induce alignment of polymer chains along one or more preferred axes or directions into fabrication of stents.

Figure 6:
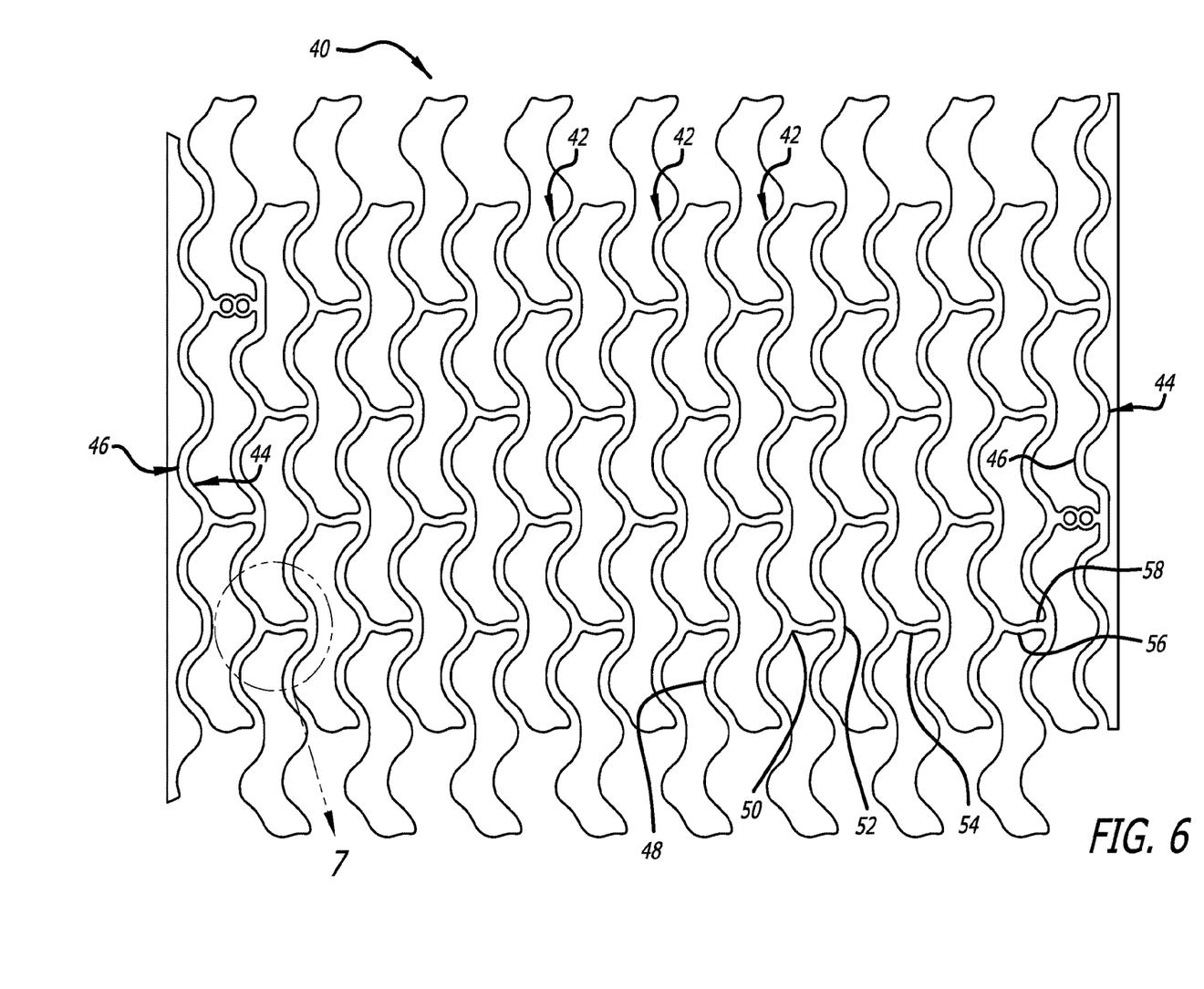
FIG. 6 is a plan view of a flattened section of one embodiment of the stent depicting curved links.

In keeping with the invention and referring to FIG. 6, stent 40 is shown in a flattened condition so that the pattern can be clearly viewed, even though the stent is in a cylindrical form in use. The stent is typically formed from a tubular member, however, it can be formed from a flat sheet such as shown in FIG. 6 and rolled into a cylindrical configuration. The stent 40 is intended to be formed of a polymer material. In one embodiment, the polymer material is processed so that the crystalline direction is primarily in the circumferential direction, thereby providing the necessary radial strength. This in part contributes to the Y-link junction being a critical location for fatigue. The design improvements disclosed herein improve the fatigue performance of the critical Y-link junction.

As shown in FIG. 6, stent 40 is made up of a plurality of cylindrical rings 42 which extend circumferentially around the stent when it is in a tubular form. Each cylindrical ring 42 has a cylindrical ring distal end 44 and a cylindrical ring proximal end 46. Typically, since the stent is laser cut from a tube, there are no discreet parts such as the described cylindrical rings and links. However, it is beneficial for identification and reference to various parts to refer to the cylindrical rings and links and other parts of the stent as follows. Each cylindrical ring 42 is comprised of U-shaped members 48, Y-shaped members 50, and W-shaped members 52. Undulating links 54 attach adjacent rings and form part of the Y-shaped members and the W-shaped members.

Each cylindrical ring 42 defines a cylindrical plane which is a plane defined by the distal and proximal ends 44, 46 of the ring and the circumferential extent as the cylindrical ring travels around the cylinder. Each cylindrical ring includes cylindrical outer wall surface which defines the outermost surface of the stent, and cylindrical inner wall surface which defines the innermost surface of the stent. The cylindrical plane follows the cylindrical outer wall surface.

The undulating links 54 are positioned within the cylindrical plane. In FIG. 6, the undulating portion of the link is positioned between adjacent rings. The undulating links connect one cylindrical ring to an adjacent cylindrical ring and contribute to the overall longitudinal flexibility of the stent due to their unique construction. The flexibility of the undulating links derives in part from a curved portion 56 connected to a straight portion 58, wherein the straight portion is substantially parallel to the longitudinal axis of the stent. Thus, as the stent is being delivered through a tortuous vessel, such as a coronary artery, the curved portions 56 of the undulating links 54 will permit the stent to flex in the longitudinal direction which substantially enhances delivery of the stent to the target site. In contrast, a straight portion 58 is parallel to the stent axis and has no curved portion, therefore it is not as flexible as the curved portion and does not add to the flexibility of the stent. An important feature of the present invention is to increase the structural fatigue performance of the links in view of the arterial curvature when the stent is implanted in a coronary artery.

Figure 7:
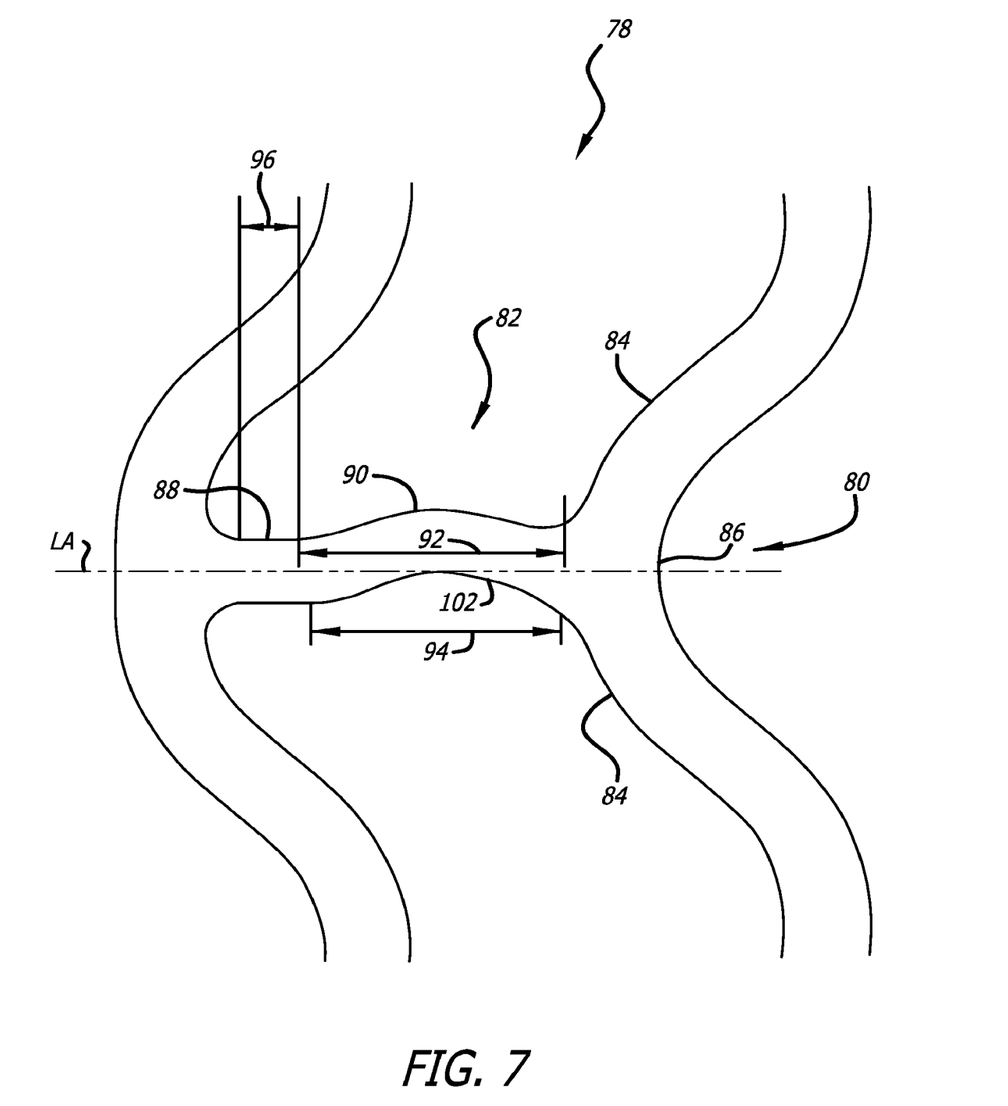
FIG. 7 is an enlarged partial view of a Y-shaped member depicting features of the invention including a link having a straight portion and a curved portion.

In one embodiment, as shown in FIG. 7, the stent section 78 has a Y-shaped member 80 formed by a link 82 attaching to the curved portion 84 of a valley 86, which then resembles the Y-shaped member. In this embodiment, each link 82 has straight section 88 and a curved section 90. The curved section 90 extends in a circumferential direction. The curved section 90 has a first curved length 92 and a second curved length 94, the first curved length being greater than the second curved length. Furthermore, the straight section 88 has a length 96 which is significantly less than both curved lengths 92 and 94 of the curved section 90. The curved section 90 in each link 82 greatly improves the fatigue resistance of the links, especially at the interface of the curved section 90 and the valley 86 of a cylindrical ring.

In one embodiment, as shown in FIG. 7, the Y-shaped members 80 are formed by links 82 attaching to the curved portion 84 of a valley 86, which then resembles the Y-shaped member. Each link has a straight section 88 and a curved section 90. The links 82 have a longitudinal axis LA bisecting the width of the links 82. In this embodiment, the curved section 90 has a width equal to the width of the links. The curved section has a first curved length 92 and a second curved length 94. The second curved length of each link forms an arc line 102, and the longitudinal axis LA that bisects the width of the straight section of each link is tangential to the arc line. In this embodiment, the curved section 90 is formed by bending the links 82 a distance equal to one half of the width of the links, however, the curved section 90 can have different curved lengths and still be within the invention. Of course, the links 82 are not literally bent to form the curved section 90 since the stent of the invention is formed by laser cutting a tubular member using a well-known process. Thus, reference to bending the links is for illustration purposes only. Importantly, the first curved length 92 and the second curved length 94 are comprised of curves having different radii so that the curved section provides improved link structural fatigue performance. In this embodiment, the first curved length is in the range from 0.035 inch (0.89 mm) to 0.028 inch (0.71 mm) and the second curved length is in the range from 0.027 inch (0.69 mm) to 0.018 inch (0.46 mm). In one preferred embodiment, the first curved length is 0.027 inch (0.68 mm) and the second curved length is 0.024 inch (0.60 mm). For one embodiment, in fatigue testing comparing a straight link versus the present invention with a curved section 90 in the links 82, there was a 23% increase in the links' structural fatigue performance.

Figure 8A:
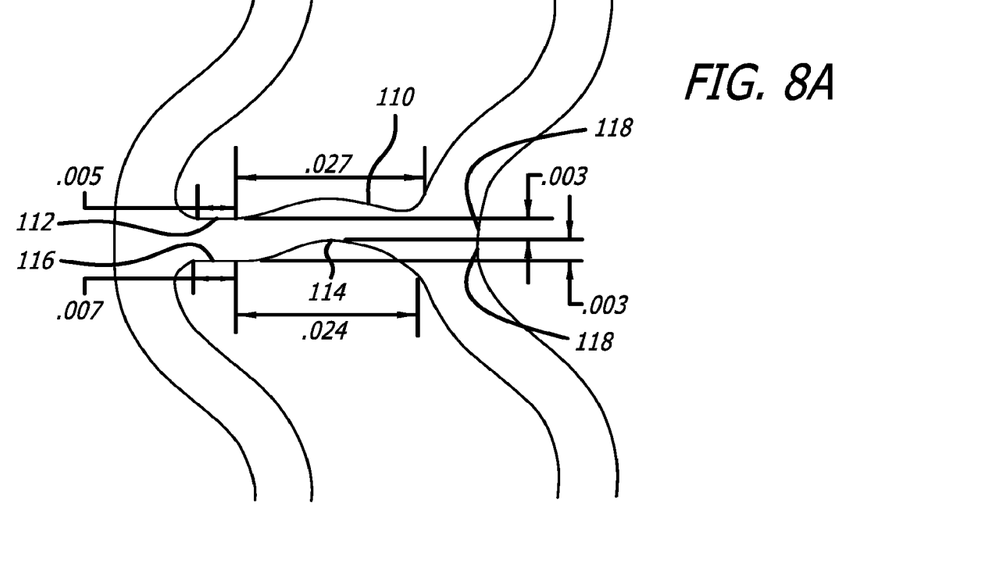
FIG. 8A is an enlarged partial view of a Y-shaped member depicting the lengths of the bends and the straight sections of the link.

In an embodiment shown in FIG. 8A, the length dimensions for the structural bends in the links are disclosed. The length along the longitudinal stent axis of the link outer radius 110 is 0.027 inch (0.68 mm); the length of the link outer straight portion 112 is 0.005 inch (0.13 mm); the length of the link inner radius 114 is 0.024 inch (0.60 mm); the length of the link inner straight portion 116 is 0.007 inch (0.17 mm); and the distance moving circumferentially from the inner straight portion 116 to the inner peak 118 of the inner radius is 0.003 inch (0.08 mm) Further, the distance moving circumferentially from the inner peak 118 to the outer straight portion 112 is also 0.003 inch (0.08 mm) These lengths, coupled with the various radii disclosed herein, provide for undulating links having increased fatigue performance.

Figure 8B:
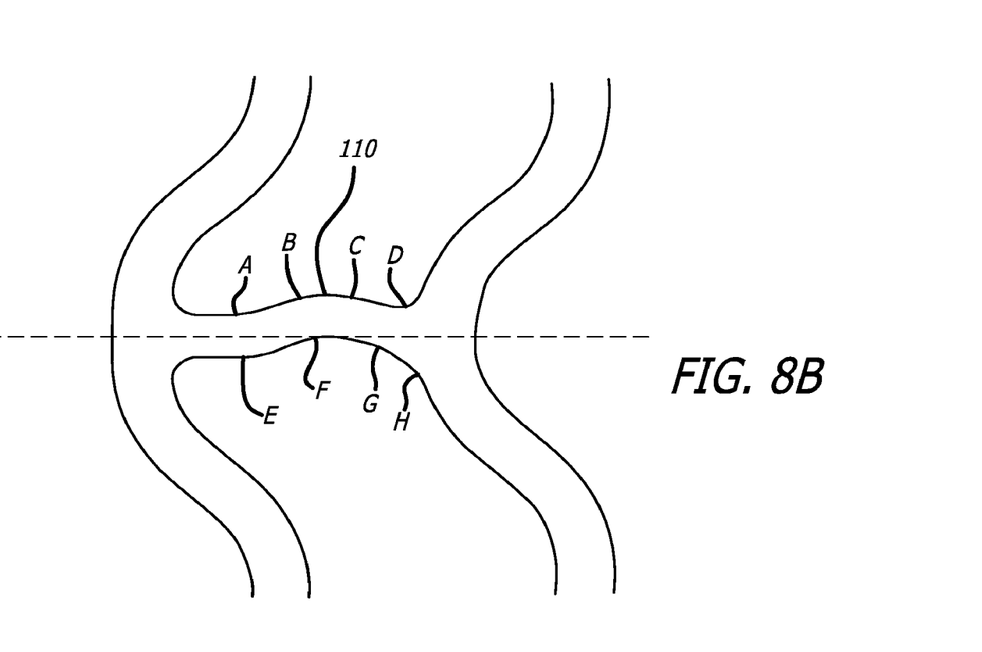
FIG. 8B is an enlarged partial view of a Y-shaped member depicting the radii of the curved portions of the link.

Referring to FIG. 8B, the elements A-H represent the various radii of the undulating link 110 so that the curved section represented by elements A-H is formed by bending a straight link a distance equal to one half of the width of the link. Of course, the links are not literally bent since they are laser cut from a tube, but the result is the inner curve section (elements F and G) being essentially tangent to a line that is the longitudinal centerline of the link if it was a straight link. The strategic placement of the various radii (elements A-H) provides for undulating links 110 having increased fatigue performance. Table 1, immediately below, discloses the various radii for elements A-H.

| Element | Radius inch/mm | Length inch/mm | Distance inch/mm |
|---------|----------------|----------------|------------------|
| A | .012/0.30 | .006/0.14 | .006/0.14 |
| B | .016/0.41 | .007/0.19 | .007/0.19 |
| C | .023/0.59 | .008/0.20 | .008/0.20 |
| D | .004/0.10 | .006/0.14 | .005/0.12 |
| E | .012/0.30 | .006/0.16 | .006/0.15 |
| F | .010/0.25 | .006/0.14 | .005/0.13 |
| G | .017/0.44 | .012/0.30 | .011/0.28 |
| H | .006/0.16 | .004/0.10 | .002/0.06 |

While the invention has been illustrated and described herein in terms of its use as an intravascular stent for treating coronary arteries, it will be apparent to those skilled in the art that the stent can be used in other instances such as in treating peripheral vessels. Other modifications and improvements may be made without departing from the scope of the invention.

Other modifications and improvements can be made to the invention without departing from the scope thereof.

We claim:

1. A longitudinally flexible stent for implanting in a body lumen, comprising:
   a first cylindrical ring, a second cylindrical ring, a third cylindrical ring, up to an Nth cylindrical ring, the cylindrical rings being generally independently expandable in the radial direction and generally aligned on a common longitudinal axis;
   each of the cylindrical rings having an undulating pattern of peaks and valleys, the undulating pattern of each of the cylindrical rings being in phase with the undulating pattern of each of the adjacent cylindrical rings;
   each of the cylindrical rings being interconnected by links to one of the adjacent cylindrical rings so that the cylindrical rings form a longitudinally flexible stent; and
   each of the links having a straight section and a curved section, the curved section having a first curved length and a second curved length; and
   wherein the second curved length of each link forms an arc line, and a longitudinal axis that bisects the width of the straight section of each link is tangential to the arc line.

2. The stent of claim 1, wherein the straight section of each link has a length, and the curved section has a length, the length of the curved section being greater than the length of the straight section.

3. The stent of claim 2, wherein the first curved length of each link is greater than the second curved length.

4. The stent of claim 2, wherein the links have a width that is uniform along the straight section and the curved section.

5. The stent of claim 3, wherein the first curved length is 0.027 inch (0.68 mm) and the second curved length is 0.024 inch (0.60 mm).

6. The stent of claim 3, wherein the first curved length is in the range from 0.035 inch (0.89 mm) to 0.028 inch (0.71 mm), and the second curved length is in the range from 0.027 inch (0.69 mm) to 0.018 inch (0.46 mm).

7. The stent of claim 1, wherein the curved section of each link is in a circumferential direction.

8. The stent of claim 1, wherein the distance between adjacent cylindrical rings is more than a width of either a single peak or a single valley.

* * * * *